(12) United States Patent
Blakstvedt et al.

(10) Patent No.: US 8,016,814 B2
(45) Date of Patent: Sep. 13, 2011

(54) GUIDEWIRES AND DELIVERY CATHETERS HAVING FIBER OPTIC SENSING COMPONENTS AND RELATED SYSTEMS AND METHODS

(75) Inventors: Adam Blakstvedt, Big Lake, MN (US); Jesus Casas, Brooklyn Park, MN (US); Timothy Robinson, Savage, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 29 days.

(21) Appl. No.: 12/045,120

(22) Filed: Mar. 10, 2008

(65) Prior Publication Data

US 2009/0227952 A1    Sep. 10, 2009

(51) Int. Cl.
*A61M 31/00* (2006.01)
(52) U.S. Cl. .......... 604/508; 604/503; 600/481
(58) Field of Classification Search .......... 600/342, 600/424, 117, 160, 182, 300, 310, 477–478, 600/481; 604/511, 510, 503, 506–508; 606/80, 606/167
See application file for complete search history.

(56) References Cited

U.S. PATENT DOCUMENTS

| | | | |
|---|---|---|---|
| 4,945,895 A * | 8/1990 | Takai et al. .......... 600/104 |
| 5,423,321 A | 6/1995 | Fontenot |
| 5,607,419 A | 3/1997 | Amplatz et al. |
| 5,830,222 A | 11/1998 | Makower |
| 5,836,940 A | 11/1998 | Gregory |
| 6,068,638 A | 5/2000 | Makower |
| 6,159,225 A | 12/2000 | Makower |
| 6,190,353 B1 | 2/2001 | Makower et al. |
| 6,283,951 B1 | 9/2001 | Flaherty et al. |
| 6,296,608 B1 * | 10/2001 | Daniels et al. .......... 600/104 |
| 6,375,615 B1 | 4/2002 | Flaherty et al. |
| 6,508,824 B1 | 1/2003 | Flaherty et al. |
| 6,544,230 B1 | 4/2003 | Flaherty et al. |
| 6,579,311 B1 | 6/2003 | Makower |
| 6,602,241 B2 | 8/2003 | Makower et al. |
| 6,655,386 B1 | 12/2003 | Makower et al. |
| 6,660,024 B1 | 12/2003 | Flaherty et al. |
| 6,685,648 B2 | 2/2004 | Flaherty et al. |
| 6,697,667 B1 | 2/2004 | Lee et al. |
| 6,709,444 B1 | 3/2004 | Makower |
| 6,726,677 B1 | 4/2004 | Flaherty et al. |

(Continued)

OTHER PUBLICATIONS

Thiagrajah, J.R. et al. "Noninvasive Early Detection of Brain Edema in Mice by Near-Infrared Light Scattering:" Journal of Neuroscience Research 80:293-299 (2005).

(Continued)

*Primary Examiner* — Theodore J Stigell (57) ABSTRACT

Methods, systems and devices for delivering a diagnostic or therapeutic treatment, substance or device to a target area located within the body of a human or animal subject. A tissue penetrating catheter is positioned within a body lumen near the target area. A hollow penetrator is then advanced from the tissue penetrating catheter and penetrated from the body lumen in which the penetrating catheter is positioned into tissue in the direction of the target area. Thereafter, an elongate optical device (e.g., an optically equipped guidewire or catheter) is advanced through the hollow penetrator and continues to advance through tissue, in the direction of the target area. The elongate optical device is connected to an optical processing device (e.g., a spectrometer) which provides optically determined data (e.g., spectral reflectance, pH, oxygen concentration, temperature) indicating when the elongate optical device has entered the target area. The elongate optical device is then used to facilitate delivery of a diagnostic or therapeutic modality, substance or device into the target area.

10 Claims, 8 Drawing Sheets

U.S. PATENT DOCUMENTS

| | | | |
|---|---|---|---|
| 6,746,464 | B1 | 6/2004 | Makower |
| 6,869,430 | B2 * | 3/2005 | Balbierz et al. ............... 606/41 |
| 6,936,033 | B2 * | 8/2005 | McIntosh et al. ............. 604/191 |
| 7,192,427 | B2 * | 3/2007 | Chapelon et al. ............... 606/33 |
| 7,209,605 | B2 | 4/2007 | Cantin et al. |
| 7,273,056 | B2 | 9/2007 | Wilson et al. |
| 2004/0162548 | A1 | 8/2004 | Reiser |
| 2005/0209564 | A1 | 9/2005 | Bonner et al. |
| 2005/0251233 | A1 | 11/2005 | Kanzius et al. |
| 2005/0251234 | A1 | 11/2005 | Kanzius et al. |
| 2005/0273143 | A1 | 12/2005 | Kanzius et al. |
| 2006/0041242 | A1 | 2/2006 | Stypulkowski |
| 2006/0190063 | A1 | 8/2006 | Kanzius |
| 2007/0021730 | A1 * | 1/2007 | Flaherty et al. ............... 604/506 |
| 2007/0142714 | A1 * | 6/2007 | Shumate et al. ............... 600/300 |
| 2007/0250139 | A1 | 10/2007 | Kanzius |

OTHER PUBLICATIONS

Merrit, et al. Coregistration of Diffuse Optical Spectroscopy and Magnetic Resonance Imaging in a Rat Tumor Model: Appl Opt. 1;42(16):2951-9 (Jun. 2003).

Nighswander-Rempel et al. :Regional Variations in Myocardial Tissue Oxygenation Mapped by Near-Infrared Spectroscopic Imagin J. Mol Cell Cardiology; 34(9):1195-203 (Sep. 2002).

Cuccia et al. In Vivo Quantification of Optical Contrast Agent Dynamics in Rat Tumors by Use of Diffuse Optical Spectroscopy With Magnetic Resonance Imaging Coregistration: Appl Opt. 1;42(16): 2940-50 (Jun. 2003).

* cited by examiner

GUIDEWIRES AND DELIVERY CATHETERS HAVING FIBER OPTIC SENSING COMPONENTS AND RELATED SYSTEMS AND METHODS

FIELD OF THE INVENTION

The present invention relates generally to methods and apparatus for medical treatment and more particularly to methods and devices useable for catheter-based delivery of substances or devices to certain sites within the body.

BACKGROUND

It is sometimes desirable to insert a medical device (e.g., a catheter, needle, cannula or other delivery device) into a particular target area (e.g., within a certain type of tissue, a lesion, tumor, necrotic or infracted area, etc.) within the body of a human or animal subject. For example, when it is desired to deliver a diagnostic or therapeutic modality or substance (e.g., dye, a drug, a biologic, cells, a gene therapy preparation, nutrients, radiation, heat, etc.) or a device (e.g., an electrode, sensor, substance delivery device, etc.) to a particular target location within a subject's body, a catheter, needle, cannula or other delivery apparatus may be inserted and advanced through the body until it is positioned within the target area. Thereafter, the diagnostic or therapeutic modality, substance or device is delivered into the target area via that catheter, needle, cannula or other delivery apparatus. In some cases, the medical device (e.g., a catheter, needle, cannula or other delivery device) is inserted directly from a location outside the subject's body and into the target area. In other cases, an intervening device may be used to facilitate such placement of the medical device. For example, in some procedures, a penetration catheter is initially inserted into the subject's vasculature and advanced into a blood vessel near the target area. A penetrator (e.g., a hollow needle) is then advanced from the penetration catheter into tissue adjacent to the blood vessel lumen in the general direction of the target area and the catheter, needle, cannula or other delivery apparatus is then advanced through the penetrator, through intervening tissue and into the target area. Examples of such procedures include those described in U.S. Pat. Nos. 5,830,222 (Makower), 6,068,638 (Makower), 6,159,225 (Makower), 6,190,353 (Makower, et al.), 6,283,951 (Flaherty, et al.), 6,375,615 (Flaherty, et al.), 6,508,824 (Flaherty, et al.), 6,544,230 (Flaherty, et al.), 6,579,311 (Makower), 6,602,241 (Makower, et al.), 6,655,386 (Makower, et al.), 6,660,024 (Flaherty, et al.), 6,685,648 (Flaherty, et al.), 6,709,444 (Makower), 6,726,677 (Flaherty, et al.) and 6,746,464 (Makower), the entire disclosure of each such United States patent being expressly incorporated herein by reference.

Determining when the catheter, needle, cannula or other delivery apparatus has entered the intended target area can present a challenge. In some instances, radiographic imaging can be used to determine when the target area has been entered. However, this approach requires that the target area be radiographically distinguishable from surrounding tissue. The use of radiographic guidance can also require extended fluoroscopy or multiple x-rays with the resultant expense and radiation exposure to the subject and medical personnel performing the procedure.

An optical system that is convenient and useable to guide the positioning of a catheter, cannula, needle or other medical device within a particular target area, without the use of radiation, is desirable. Preferably, such an optical system would not only sense when the catheter, cannula, needle or other medical device has entered the target area but may also be used to track the device during insertion and removal.

The prior art has included a number of optical devices which purportedly may sense the location of a catheter or device within a body. For example, U.S. Pat. No. 5,423,321 (Fontenot) describes a catheter that has multiple light guiding fibers of different lengths. The catheter is inserted into an organ or vessel and visible or near infrared light is delivered through the light guiding fibers. The light emitted from the catheter is then observed through the wall of the organ or vessel, thereby indicating the position of the catheter. A detection system is also described for determining when a surgical cutting tool approaches the vessel.

U.S. Pat. No. 7,273,056 (Wilson et al.) describes an optically guided catheter wherein a small laser diode is inserted in a distal end of the catheter and light from the laser diode is passed through an optical fiber that extends through the catheter. The light is selected to be of a wavelength that is minimally absorbed by tissue, preferably in the range from about 620 nm to 1100 nm. 780 nm is preferably used as this is where the tissue absorption is near a minimum. The light passes out the end of the fiber (at the proximal end of the catheter) and through the tissue to the outside of the patient's skin where it is measured. The light pattern is observed by night vision goggles that filter out other frequencies of light. The detected light permits location of the end of the fiber, the positional accuracy depending on the thickness of tissue between the fiber tip and the exterior of the body. The method is highly accurate for small children and for catheters within a few centimeters of the skin surface of adults.

Thus, there remains a need in the art for the development of new devices and methods for optically guided positioning of catheters, cannulae, needles and other devices within specific intracorporeal target areas.

SUMMARY OF THE INVENTION

In accordance with the present invention, there is provided a method for delivering a diagnostic or therapeutic treatment, substance or device to a target area located within the body of a human or animal subject. In general, such method comprises the steps of (A) providing an elongate optical device comprising an elongate shaft, a light transmitting fiber and a reflected light return fiber usable for optical determination of a tissue variable that distinguishes the target area from other areas, (B) providing a tissue penetrating catheter device comprising a catheter shaft that is positionable in a body lumen within the subject's body and a penetrator that is advanceable from the catheter to a location outside of the body lumen in which the catheter shaft is positioned, said penetrator having a lumen with a distal opening, (C) positioning the tissue penetrating catheter within a body lumen, (D) advancing the penetrator from the penetrating catheter to a position outside the body lumen in which the penetration catheter is positioned, (E) advancing the elongate optical device through the lumen of the penetrator, out of the distal opening and through tissue in the direction of the target area, (F) delivering light through the light transmitting fiber and using reflected light received from the reflected light return fiber to measure said tissue variable, (G) determining when said tissue variable indicates that the elongate optical device is within the target area and (H) using the elongate optical device to facilitate delivery of a diagnostic or therapeutic modality, substance or device into the target area.

Further in accordance with the present invention, there is provided a system that is useable to perform the above-summarized method. In general, such system comprises (A) a penetrating catheter device comprising an elongate catheter shaft and a penetrator having a lumen, said penetrator being advanceable from the catheter shaft and (B) an elongate optical device comprising an elongate shaft, a light transmitting fiber and a reflected light return fiber usable for optical determination of a tissue variable that distinguishes the target area from other areas, said elongate optical device being advanceable though the lumen of the penetrator.

Still further in accordance with the present invention, the elongate optical device may be any type of elongate device useable to facilitate delivery of a diagnostic or therapeutic modality, substance or device into the target area. For example, in some cases, the elongate optical device may comprise a guidewire. After such guidewire has been advanced into the target area, one or more other treatment devices (e.g., catheters) may then be advanced over the guidewire and used to deliver a desired therapy, substance or device to the target area. In other cases, the elongate optical device may be a delivery catheter that is itself useable, after having been advanced into the target location, to deliver a desired therapy, substance or device to the target area.

Further aspects, details and embodiments of the present invention will be understood by those of skill in the art upon reading the following detailed description of the invention in conjunction with the accompanying drawings.

DETAILED DESCRIPTION

The following detailed description and the accompanying drawings are intended to describe some, but not necessarily all, examples or embodiments of the invention. The contents of this detailed description and accompanying drawings do not limit the scope of the invention in any way.

The present invention provides methods, systems and devices (e.g., guidewires and catheters) that utilize optical sensing (e.g., reflectance spectrometry) to distinguish specific tissues of the body (e.g., tissues affected by inflammation, infection, ischemia, hyperproliferation or neoplasia, necrosis, edema, etc.) from other tissues or anatomical structures, thereby facilitating targeted delivery of a desired treatment, device or substance into a specific type of target tissue.

Figure 1:
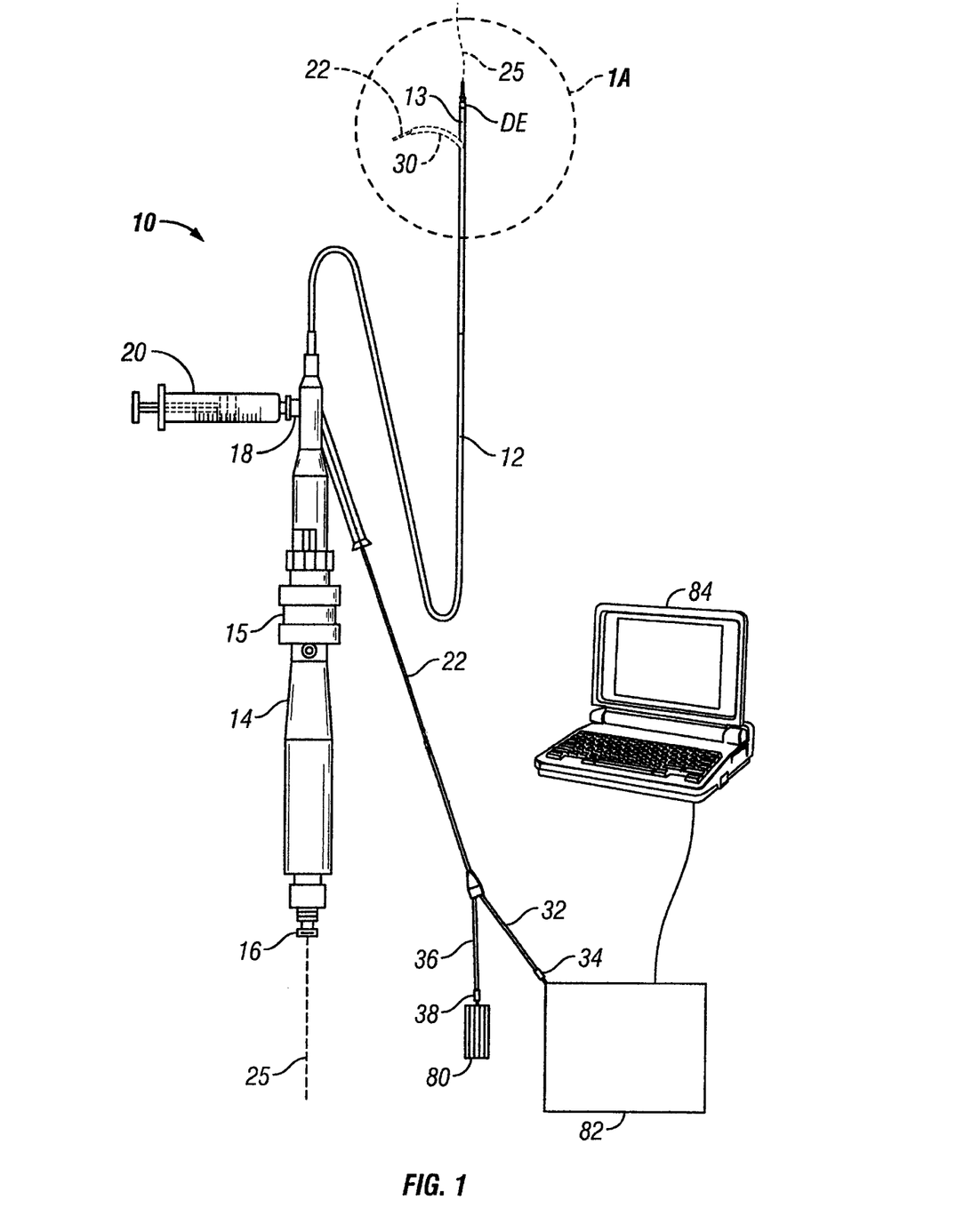
FIG. 1 is a side view of a system of the present invention comprising a tissue penetrating catheter in combination with an optical sensor equipped elongate device (e.g., guidewire or catheter).

FIG. 1 shows an example of a system 10 of the present invention. This system 10 generally comprises a tissue penetrating catheter device having a handpiece 14, a catheter body 12 and a penetrator 30 that is advanceable from the catheter body 12, in combination with an elongate optical device 22 (e.g., a guidewire or delivery catheter) that is advanceable through the penetrator 30 into tissue that lies ahead of the penetrator 30. The proximal end of the elongate optical device 22 is attached to a light source 80 and a spectrometer 82 or other reflected light processing device capable of converting light that has been reflected from tissue into discern information about the tissue. The spectrometer 82 or other processing device may be connected to a computer 84 that is programmed to further process, analyze and/or display information received from the spectrometer 82 or other processing device.

Some embodiments of the invention may operate on the basis of reflectance spectroscopy, which is the study of light as a function of wavelength that has been reflected or scattered from a solid, liquid, or gas. In embodiments which operate on the basis of reflectance spectrometry, light from the light source 80 travels in the distal direction through elongate optical device 22 and out of the distal end of the elongate optical device 22. Reflected light then travels in the proximal direction through the elongate optical device 22 and is received by the spectrometer 82. Signals from the spectrometer 82 are then received by a computer 84 or other monitor/display device which then processes those signals and displays the absorptivity spectra measured by the spectrometer in a graphic or other suitable format. Various types of reflectance spectroscopy (e.g., visible light, infrared light, ultraviolet light, etc.) may be employed, depending on the types of tissues and/or body fluids through which the elongate optical device 22 will advance. In some embodiments, such as those where it is desired to distinguish infarcted cardiac tissue from non-infarcted cardiac tissue, the light source 80 may emit near infrared light (e.g., Model HL-2000 tungsten light source available from Ocean Optics, Inc., 830 Douglas Ave, Dunedin, Fla. 34698) and the spectrometer 82 may be a near infrared spectrometer (e.g., Model USB 4000 NIR Spectrometer available from Ocean Optics, Inc., 830 Douglas Ave, Dunedin, Fla. 34698).

Tissue Penetrating Catheter

Figure 1A:
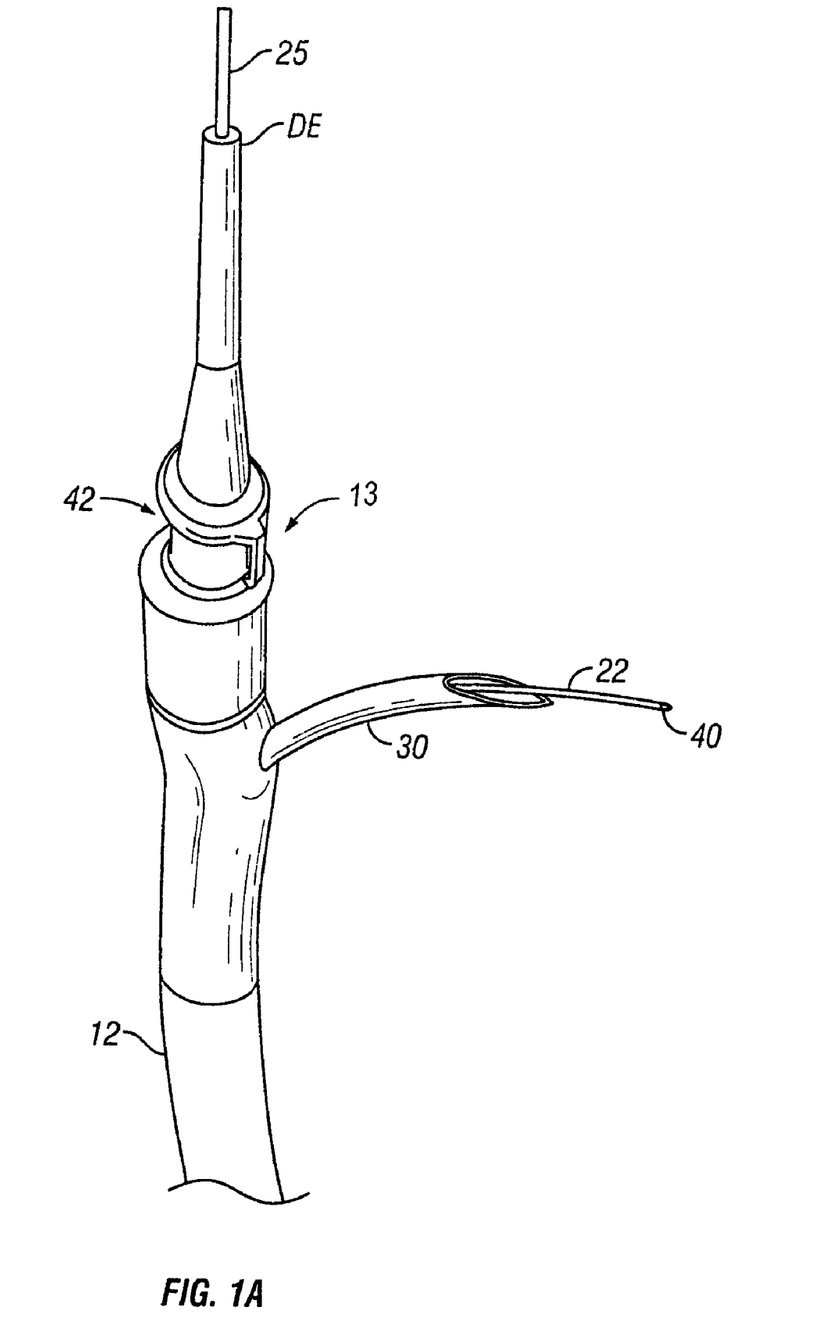
FIG. 1A is an enlarged view of area 1A of FIG. 1.

As seen in FIG. 1, the tissue penetrating catheter may have a lumen which extends from a guidewire insertion port 16 on the proximal end of the handpiece 14 through on opening on the distal end DE of the catheter body 12 to allow the tissue penetrating catheter to be advanced over a guidewire 25. Such lumen may also have a port 18 to which a syringe 20 or other infusion apparatus may be attached to facilitate injection or infusion radiographic contrast fluid, saline solution, medicaments or other fluids through that lumen. A penetrator control knob 15 may be provided on the handpiece 14 to allow the operator to control the advancement and retraction of the penetrator 30. The penetrator 30 may comprise a straight or curved hollow needle that advances in a lateral direction from the body 12 of the tissue penetrating catheter as shown in FIGS. 1 and 5A-5D. As seen in FIG. 1A, the tissue penetration catheter may optionally incorporate an orientation system 13 which is useable to predict the trajectory or direction in which the penetrator 30 will subsequently advance from the catheter body while the penetrator 30 is still in its retracted position within the catheter body. This allows the operator to adjust the rotational orientation of the catheter body 12 prior to advancement of the penetrator 30 so that when the penetrator 30 is subsequently advanced from the catheter body 12 it will advance into the target area and not to some other area. In some embodiments, this orientation system 13 may comprise an intravascular ultrasound imaging apparatus 42 capable of imaging the target area TA in conjunction with an indicator (e.g., an ultrasound echo, pointer, electronic indicator, etc.) that provides on the ultrasound image an indicator of the predicted trajectory on which the penetrator 30 will subsequently advance. Alternatively, the orientation system 13 may comprise one or more radiographic markings that may be viewed by fluoroscopy or x-ray and which indicate the radial direction in which the penetrator 30 will subsequently advance from the catheter body 12. Examples of such orientation systems 13 are fully described in U.S. Pat. Nos. 5,830,222 (Makower), 6,068,638 (Makower), 6,159,225 (Makower), 6,190,353 (Makower, et al.), 6,283,951 (Flaherty, et al.), 6,375,615 (Flaherty, et al.), 6,508,824 (Flaherty, et al.), 6,544,230 (Flaherty, et al.), 6,579,311 (Makower), 6,602,241 (Makower, et al.), 6,655,386 (Makower, et al.), 6,660,024 (Flaherty, et al.), 6,685,648 (Flaherty, et al.), 6,709,444 (Makower), 6,726,677 (Flaherty, et al.) and 6,746,464 (Makower), the entire disclosure of each such United States patent being expressly incorporated herein by reference. Also, one commercially available example of such a tissue penetrating catheter is the Pioneer™ catheter available from Medtronic Cardiovascular, Inc., Santa Rosa, Calif.

Elongate Optical Device

The elongate optical device 22 is advanceable out of the open distal end of the penetrator 30 and delivers light from a light source 80 into tissue adjacent to the distal end of the elongate optical device 22. It also transmits reflected light from the tissue back to the spectrometer 82. Such elongate optical device 22 may be of non-tubular construction (e.g., a probe or guidewire) or it may be tubular (e.g., a catheter having one or more lumens). In some embodiments, the elongate optical device 22 may include the above-described optical guidance capabilities as well as the ability to emit an energy based treatment (e.g., laser, radiofrequency energy, other electromagnetic energy, heat, phototherapy, force, pressure, etc.) directly into the target tissue into which it has been advanced. In other embodiments, such as the example shown in FIGS. 2-2C, the elongate optical device 22 may comprise a guidewire 22a that that includes the above-described optical guidance capabilities so that it may be advanced under optical guidance into a particular target tissue and is then used to guide the advancement of another catheter or other device into that target tissue. In still other embodiments, such as those shown in FIGS. 3-3C and 5A-5D, the elongate optical device 22 may comprise a catheter that includes the above-described optical guidance capabilities as well as delivery lumen(s) or other delivery apparatus to deliver a desired device (e.g., an electrode or implantable device) or substance(s) into the target tissue.

Optically Guided Guidewire Embodiment

Figures 2, 2A, 2B, 2C:
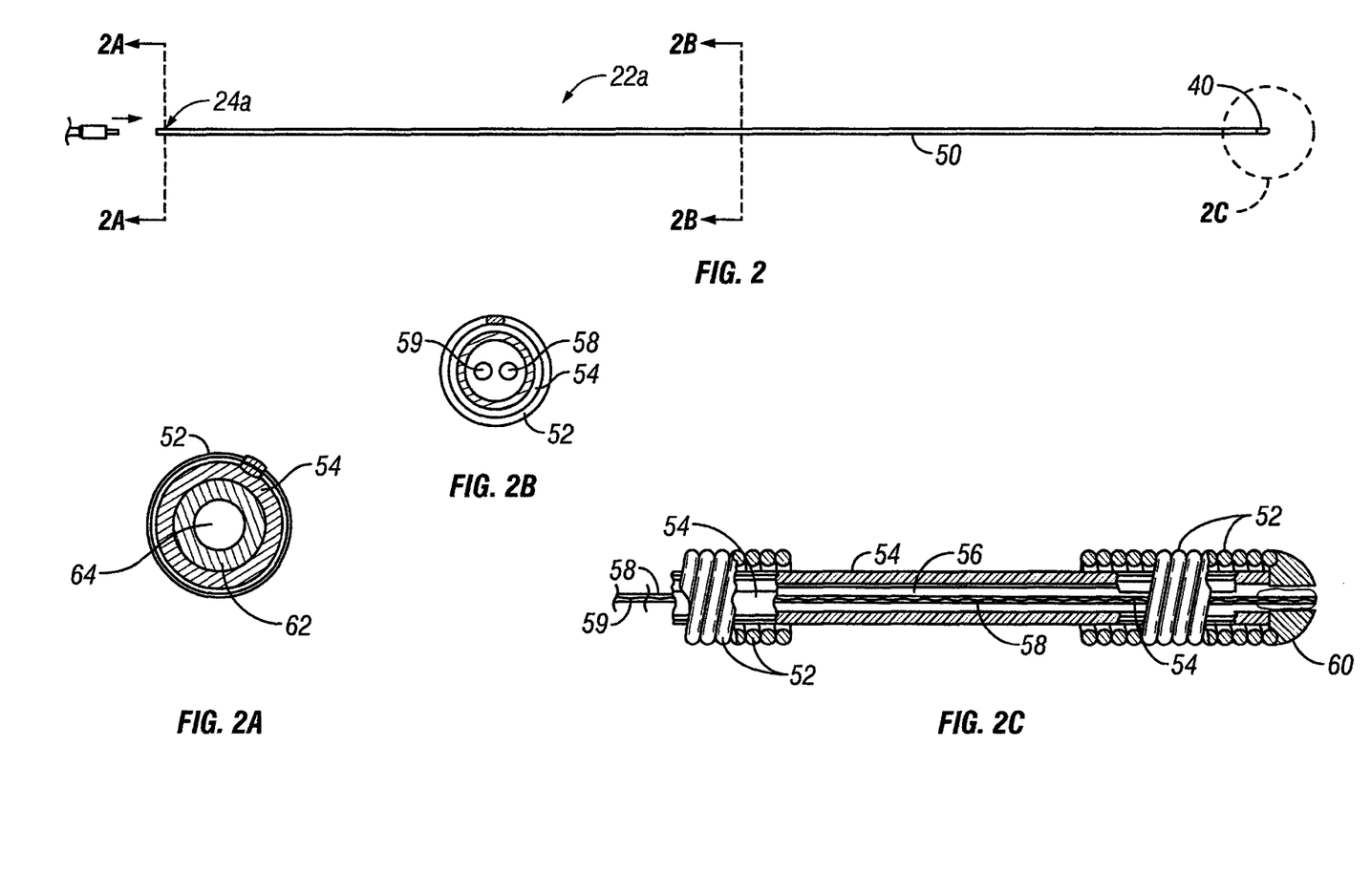
FIG. 2 is a side view of an optical sensor equipped guidewire device of the present invention.
FIG. 2A is a cross-sectional view through line 2A-2A of FIG. 2.
FIG. 2B is a cross sectional view through line 2B-2B of FIG. 2.
FIG. 2C is an enlarged view of area 2C of FIG. 2.

In the particular example of FIGS. 2-2C, the elongate optical device 22 comprises a guidewire 22a. This optically guided guidewire 22a has an elongate shaft 50 with a light delivery fiber 58 and a reflected light return fiber 59 extending longitudinally though the shaft 50. In general, the guidewire shaft 50 comprises an outer helical wire coil 52 surrounding a tubular core 54 that has a lumen 56 extending therethrough. An end plug 60 having a bore extending longitudinally through the center thereof is affixed on the distal end of the guidewire body 50. The distal ends of both light fibers 58, 59 are polished and are affixed by adhesive or potting material, or are otherwise positioned within (or possibly extending beyond), the central bore of the end plug 60. In this manner, light that is transmitted in the distal direction through the light delivery fiber 58 will be cast into tissue located distally adjacent the distal end of the guidewire 22b and light that has been reflected from that tissue will be received by and transmitted in the proximal direction through the reflected light return fiber 59. An optical connector 24a is located on the proximal end of the guidewire shaft 50 to facilitate connection of the guidewire 22a to a bifurcated optical cable of the type shown in FIGS. 4-4D and described below or other suitable cable which carries incoming light from the light source 80 to the light delivery fiber 58 and reflected light from the reflected light return fiber 59 to the spectrometer 82 or other processing device. This optically guided guidewire 22a may be of any suitable length, diameter and flexibility. For applications where it is desired to advance this guidewire 22a through the penetrator 30 of a penetrating catheter that has been advanced into a coronary blood vessel for the purpose of locating an infracted or diseased area of myocardium, such guidewire 22a may preferably have a length of from about 170 cm to about 190 cm, a diameter of from about 60 microns to about 180 microns and sufficient flexibility to navigate through the penetrator 30 but sufficient rigidity in at least its distal portion to advance through myocardial tissue after it has exited the distal end of the penetrator 30.

For many applications, the distal tip of the optically guided guidewire 22a may be beveled or sharpened to facilitate its advancement through tissue or, optionally, it may incorporate an emitting distal tip for enhanced tissue penetrating capability. For example, a radiofrequency electrode may be located on or near the distal tip of the guidewire 22a to provide for tissue penetration enhanced by RF energy emission. Or, alternatively, the distal tip of the guidewire 22a may be adapted to ultrasonically vibrate, thereby improving its ability to penetrate through tissue.

Optically Guided Delivery Catheter Embodiment

Figure 3:
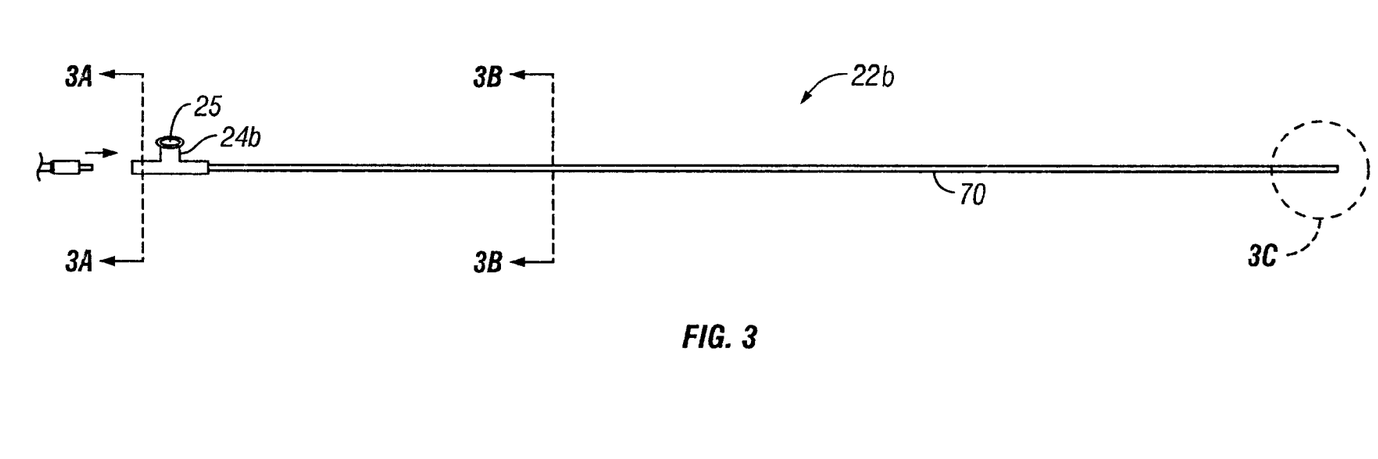
FIG. 3 is a side view of an optical sensor equipped delivery catheter of the present invention.
Figure 3A:
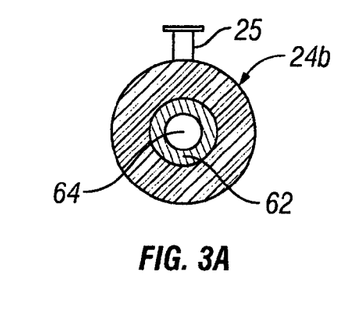
FIG. 3A is a cross-sectional view through line 3A-3A of FIG. 3.
Figure 3B:
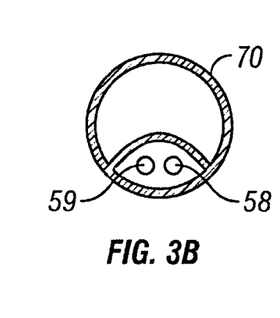
FIG. 3B is a cross sectional view through line 3B-3B of FIG. 3.
Figure 3C:
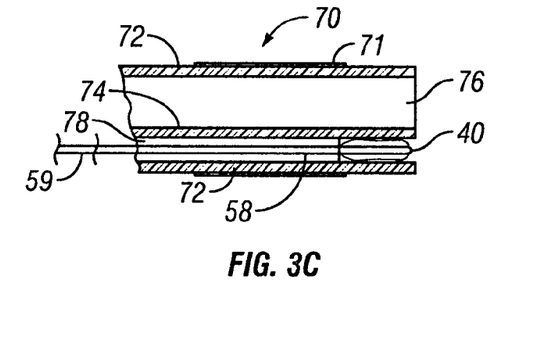
FIG. 3C is an enlarged view of area 3C of FIG. 3.

In the particular example of FIGS. 3-3C, the elongate optical device 22 comprises a delivery catheter 22b that has an elongate catheter shaft 70 with one or more working lumen(s) 76 separated by a bulkhead 74 from an optical fiber lumen 78. A light delivery fiber 58 and a reflected light return fiber 59 extend longitudinally though the optical fiber lumen 78. The distal ends of both of these fibers 58, 59 are polished and are affixed by adhesive, potting material or otherwise positioned within (or possibly extending beyond) the distal end of the optical fiber lumen 78 such that light transmitted in the distal direction through the light delivery fiber 58 will be cast into tissue immediately adjacent the distal end of the delivery catheter 22b and light that has been reflected from that tissue will be received by and transmitted in the proximal direction through the reflected light return fiber 59. A connector 24b is located on the proximal end of the catheter shaft 70 to facilitate connection of the catheter 22b to a bifurcated optical cable, or to another suitable cable which carries incoming light from the light source 80 to the light delivery fiber 58 and reflected light from the reflected light return fiber 59 to the spectrometer 82 or other processing device. Additionally, a port 25 is formed on proximal connector 24b in communication with the working lumen(s) 76 to facilitate delivery of a substance (e.g., a drug, biologic, cells, gene therapy preparation, radiographic contrast medium, etc.) or device (e.g., wire/ electrode, substance delivery implant, sensor, etc.) through the working lumen(s) 76 and into the target tissue within which the distal end of the delivery catheter 22b has been positioned.

The optical connectors used in this system may be selected from commercially available optical connectors, such as those available from Ocean Optics, Inc., 830 Douglas Ave, Dunedin, Fla. 34698.

Examples of substances that may be delivered through the working lumen(s) 76 include but are not limited to drugs (thrombolytics, platelet inhibitors, anti-restenotic agents, beta blockers, ion channel antagonists, positive or negative ionotropic agents, anti-arrhythmics, antibiotics, analgesics, chemotherapeutic agents, other anti-neoplastic agents, etc.), natural or recombinant proteins (e.g., angiogenic proteins such as vascular endothelial growth factor (VEGF), fibroblast growth factors (FGF), epidermal growth factor (EGF), platelet-derived growth factor (PDGF) nerve cell growth factor (NGF) or hepatocyte growth factor (HGF)), cells or cellular preparations (e.g., stem cells (adult or embryonic), other progenotor cells, myocytes, myoblasts, pancreatic islet cells, dopamine secreting cells, genes or gene therapy preparations (e.g., viral vectors containing genes for gene therapy applications, genetic material for electrophoretic transmission into cells, plasmids, viral vectors, genetically modified cells, naked DNA, etc.), contrast media or dyes for imaging, fillers or bulking agents (e.g., collagen, hyaluronic acid, other glycosaminoglycans), radio-labeled diagnostic materials or drugs or other traceable substances, radioactive pellets, radiotherapy preparations, mixtures of any of the above, alone, in solution or in combination with any delivery substance or matrix (e.g., polymer matrices used to inhibit or slow distribution or dissemination of a substance away from its original injection site), dialysis solutions or micro-dialysis solutions, or any other type of substances that may be introduced through the delivery catheter for any therapeutic, imaging, diagnostic or other purpose. Additionally, the delivery catheter 22b may be used for targeted delivery of radiofrequency absorption enhancers (e.g., carbon nanoparticles) into tumors or other unwanted tissue and radiofrequency energy may then be passed through the tissue resulting in therapeutic heating or, if desired, thermal necrosis/ablation of tissue within the area where the radiofrequency absorption enhancer has been delivered. Examples of such therapies are described in United States Patent Application Publications No. 2007/0250139 (Kanzius) entitled *Enhanced Systems And Methods For RF-Induced Hyperthermia II,* 2006/0190063 (Kanzius) entitled *Enhanced Systems And Methods For RF-Induced Hyperthermia;* 2005/0273143 (Kanzius et al.) entitled *Systems And Methods For Combined RF-Induced Hyperthermia And Radioimmunotherapy;* 2005/0251234 (Kanzius et al.) entitled *Systems And Methods For RF-Induced Hyperthermia Using Biological Cells And Nanoparticles As RF Enhancer Carriers* and 2005/0251233 (Kanzius) entitled *System And Method For RF-Induced Hyperthermia,* the entire disclosures of each such published patent application being expressly incorporated herein by reference.

Although FIGS. 3-3C show an embodiment of the delivery catheter 22b having a single working lumen 76, it is to be appreciated that the delivery catheter 22b may alternatively have two or more working lumens 76. Such a catheter 22b having two or more working lumens 76 may be used for the simultaneous introduction of separate streams of component substances such that the component substances become combined as they exit the catheter 22b and/or within the target tissue to form a resultant substance. One example of a multiple component substance that may be formed in situ in this manner is platelet gel (PG) or autologus platelet gel (APG). PG and APG, when delivered directly into myocardial tissue, have been shown the improve cardiac function and/or to prevent deleterious ventricular remodeling following myocardial infarction or other injury to the myocardium as described in parent U.S. patent application Ser. No. 11/426,219 and in United States Patent Application Publication Nos. 2006/0041242 and 2005/209564, the entire disclosures of which are expressly incorporated herein by reference. In this therapy, a platelet-containing component (e.g., platelet rich plasma (PRP)) is combined with a thrombin-containing component (e.g, a thrombin solution) immediately before, during or after injection into the myocardium at one or more location(s) within or near the infarct or other myocardial injury. The platelet-containing component (e.g., PRP) combines with the thrombin-containing component and forms a platelet gel (PG) which causes the desired therapeutic effect. Such PG is formed when platelets contained in the platelet-containing component are activated by thrombin contained in the thrombin-containing component. Autologous PRP can be obtained from the subject's own blood, thereby significantly reducing the risk of adverse reactions or infection. When autologous PRP is used as the platelet-containing component, the resultant PG is referred to as autologous platelet gel (APG). The addition of thrombin to platelet-containing plasma products such as PRP is described in detail in U.S. Pat. No. 6,444,228, the disclosure of which is expressly incorporated herein by reference. PRP has also been used in a variety of orthopedic and other applications.

Other examples of multiple component substances that may be formed in situ using a catheter 22b having two or more working lumens 76 include but are not limited to: multiple component tissue adhesives and sealants (e.g., Tisseel VH™ Fibrin Sealant, available commercially from Baxter Healthcare Corporation, Deerfield, Ill.); tissue bulking agents, fillers or polymeric materials (e.g., hydrogels) that may be formed or expanded in situ for various therapeutic or cosmetic applications such as tissue bulking, filling or expanding and various prodrug+activator combinations.

The optically guided delivery catheter 22b may be of any suitable length, diameter and flexibility. For applications where it is desired to insert the delivery catheter 22b at a femoral site and advance the delivery catheter 22b through the vasculature (e.g., through a tissue penetrating catheter or independently) and into an infracted, diseased or dysfunctional area of myocardium, such delivery catheter 22b may, in at least some embodiments, have a length of about 100 inches and may have an outer diameter of from about 0.25 mm to about 0.5 mm and will preferably have sufficient flexibility to navigate through the tortuous vasculature while at the same time having sufficient rigidity to penetrate and advance through myocardial tissue. Other catheter sizes may also be useable.

For many applications, the delivery catheter 22b may be formed of stainless steel hypotube or it may be formed of a suitable polymeric material such as polyimid, polytetrafluoroethylene, polypropylene, polyethylene, a polyether block amide (e.g., Pebax™), etc. In some embodiments, the distal tip of the delivery catheter 22b may be beveled or sharpened to facilitate its advancement through tissue or, optionally, the delivery catheter 22b may have an energy emitting distal tip for enhanced tissue penetrating capability. For example, a radiofrequency electrode may be located on or near the distal tip of the delivery catheter 22b to provide for tissue penetration enhanced by RF energy emission. Or, alternatively, the distal tip of the delivery catheter 22b may be adapted to ultrasonically vibrate, thereby improving its ability to penetrate through tissue.

Optionally, all or part of the delivery catheter 22b may be radio-opaque or one or more radio-opaque markers, such as a metallic marker band 71 seen in FIG. 3C, may be formed on the delivery catheter (e.g., at or near its distal tip) to permit imaging of the catheter and determination of the position of the catheter within the patient's body.

In some applications, such as those where drugs, substances or apparatus are to be chronically delivered to the target site over a period of days, weeks or months, the delivery catheter 22b may be allowed to remain indwelling after the penetrating catheter has been removed. To facilitate this, the proximal connector 24b may be detachable or removable so that it may be removed from the delivery catheter 22b during proximal withdrawal and removal of the vessel penetrating catheter while the delivery catheter 22b remains in place. Thereafter, the proximal end of the delivery catheter 22b may remain exteriorized and the proximal connector 24b or any other suitable connector, injection port or hub may be attached to the proximal end of the delivery catheter 22b to facilitate occasional or continuous delivery of the desired substance or apparatus through the working lumen(s) 76. Alternatively, the proximal end of the delivery catheter may be attached to a subcutaneously implanted port such that substances may be infused or injection though that subcutaneously implanted port when desired. Alternatively, in some cases, the proximal end of the delivery catheter 22b may be connected to a pump or delivery device for infusion of substance(s) through the working lumen(s) 76.

The delivery catheter may be straight or curved, as needed to accomplish the desired procedure. In some but not necessarily all cases, the delivery catheter may constitute a very small diameter catheter of a type known in the art as a microcatheter.

Figure 4:
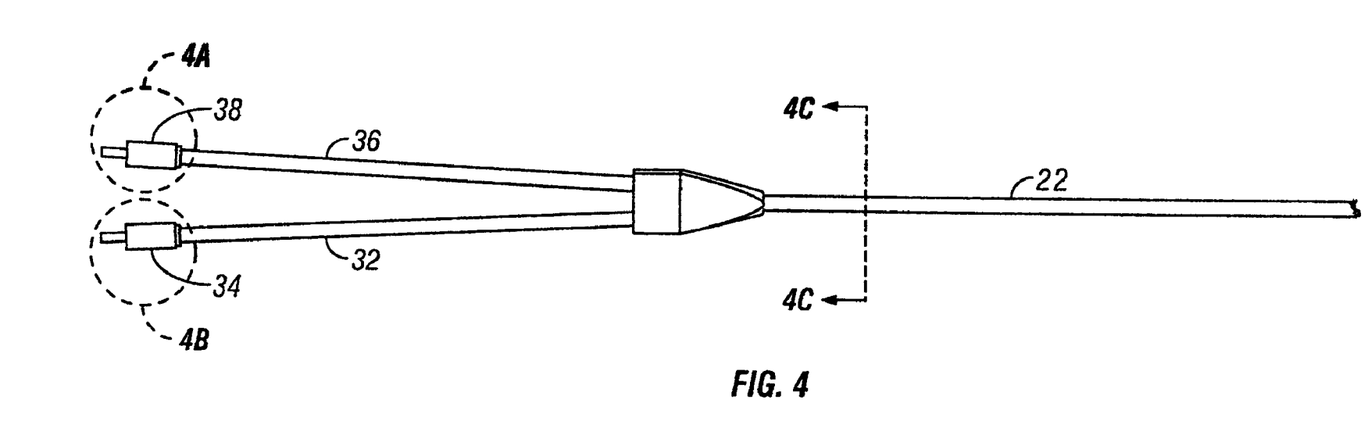
FIG. 4 is a side view of a bifurcated cable assembly usable in conjunction with the optical sensor equipped elongate device (e.g., guidewire or catheter) of the present invention.
Figure 4A:
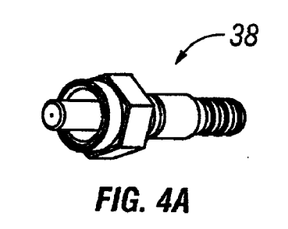
FIG. 4A is an enlarged view of area 4A of FIG. 4.
Figure 4B:
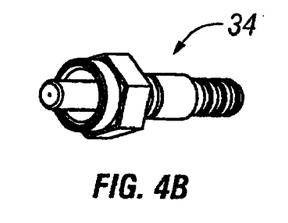
FIG. 4B is an enlarged view of area 4B of FIG. 4.
Figure 4C:
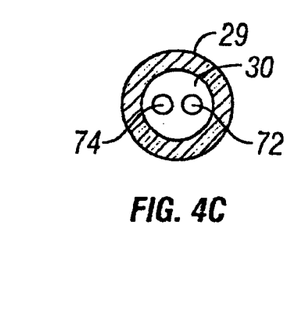
FIG. 4C is a cross sectional view through line 4C-4C of FIG. 4.

In the manner of that shown in FIG. 4, the proximal end of the elongate optical device 22 is connected to a bifurcated optical cable having a first proximal cable arm 32 and a second proximal cable arm 36. The distal portion of this bifurcated cable comprises a tube 29 having the light delivery fiber 72 and reflected light return fiber 74 extending therethrough. The reflected light return fiber 74 of the cable continues through the first proximal cable arm 32 and is connected by optical connector 34 to the spectrometer or other processing device 82. The light delivery fiber 72 of the cable continues through the second proximal cable arm 36 and is connected by optical connector 38 to the light source 80.

Methods of Use

Figure 5A:
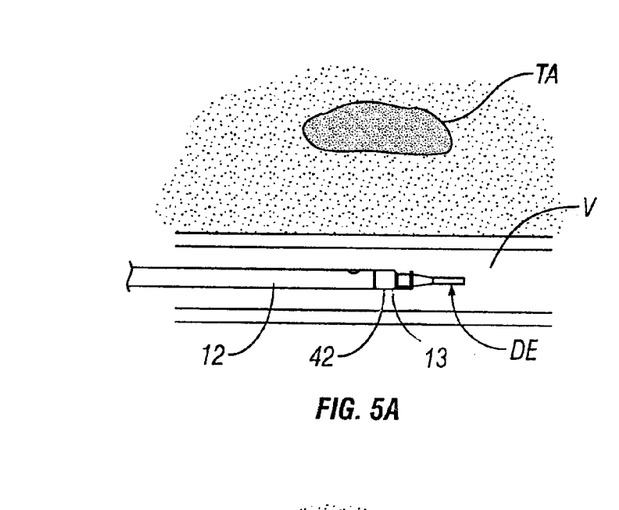
FIGS. 5A through 5D are diagrams showing steps in a transluminal method wherein the system of FIG. 1 is used to advance the optical sensor equipped elongate device (e.g., guidewire or catheter) into a desired target area within the body of a human or animal subject.
Figure 5B:
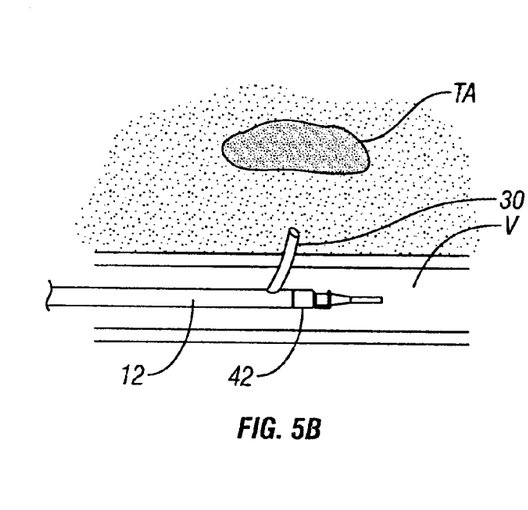
Figure 5C:
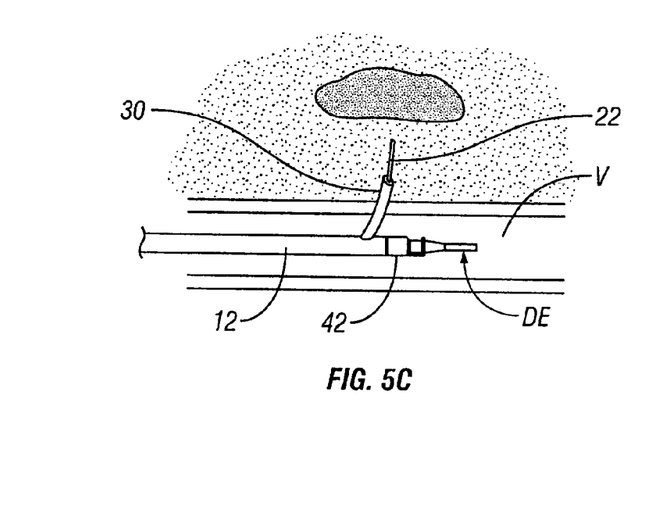
Figure 5D:
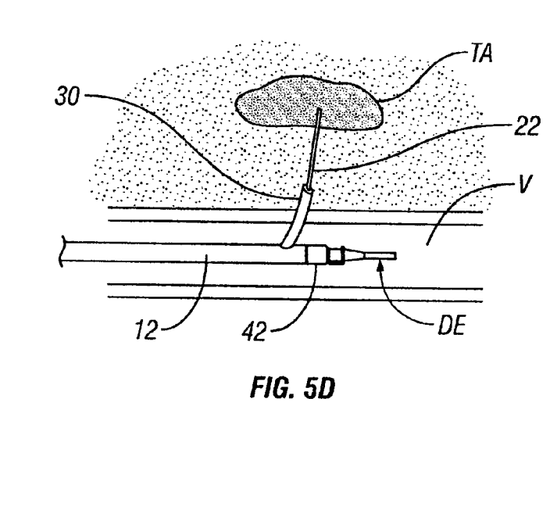

FIGS. 5A-5D show steps in a method for using the system of FIG. 1 to position the distal tip of an elongate optical device 22 within a target area TA such as a area of diseased or infracted tissue, a tumor, a particular anatomical structure or body cavity, etc. Initially, as seen in FIG. 5A, the tissue penetrating catheter body 12 is advanced though the subject's vasculature to a position within the lumen of a blood vessel V near the target area TA. If the tissue penetrating catheter is equipped with an orientation indicating system 13, such as an intravascular ultrasound apparatus 42 with accompanying indicator or radiographic markings (not shown), such orientation indicating system may be used to adjust the rotational orientation of the catheter body 12 within the vessel V as needed to ensure that, when the penetrator 30 is subsequently advanced from the catheter body 12, it will advance toward the target area TA and not in some other direction. Thereafter, as seen in FIG. 5B, the penetrator 30 is advanced from the catheter body 12 in the direction of the target area TA. Then as shown in FIG. 5C, the elongate optical device 22 is advanced through the lumen of the penetrator, out of the distal end of the penetrator and though tissue lying between the distal end of the penetrator 30 and the target area TA. Optically transmitted information (e.g., spectral reflectance, pH, oxygen saturation, temperature, etc.) is then processed by the spectrometer 82 or other processing device and computer 84 and is ultimately utilized by the operator to determine when the distal end of the elongate optical device 22 is within the target area TA as seen in FIG. 5D.

The computer 84 utilizes signals received from the spectrometer 82 or other processing device to produce a graphic display or other type of displayed information that is useable by the operator to determine when the distal end of the elongate optical device 22, 22a, 22b has been advanced into a desired target tissue type. This computer 84 may be programmed with any suitable software for this task. For example, for measurements being made in the white light range (e.g., detection of chronically infracted tissue), the computer 84 may utilize OOIBase32 software available from Ocean Optics, Inc., 830 Douglas Ave, Dunedin, Fla. 34698. Alternatively, for measurements being made in the near infrared (NIR) range (e.g., detection of acute infarctions) the computer 84 may utilize SpectraSuite™ software also available from Ocean Optics, Inc., 830 Douglas Ave, Dunedin, Fla. 34698.

Figure 6:
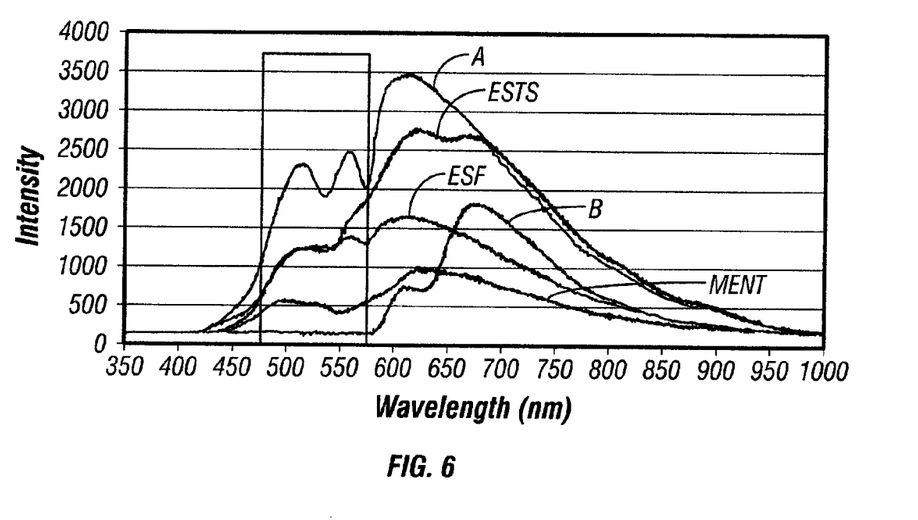
FIG. 6 is a graph showing an example of spectral reflection data generated by an optical sensor equipped catheter as it is advanced through different areas of a heart.

FIG. 6 is a graph showing data collected from an explanted pig heart. In some cases, such as illustrated in the figure, the wavelength of the light emitted from the light source 80 may be varied at intervals as the elongate optical device 22, 22a, 22b is advanced through tissue and the computer 84 may display a graph showing the intensity of the reflected light versus wavelength. As seen in FIG. 6, the intensity versus wavelength curve varies from tissue type to tissue type and, thus, such curve may provide a "signature" indicative of the light absorptive qualities of the tissue type in which the distal tip of the elongate optical device 22, 22a, 22b is currently positioned. By way of example, FIG. 6 shows intensity versus wavelength curves for the aortic wall A, a thermal scar on the epicardial surface of the heart ESTS, epicardial surface fat ESF, mid-epicardial normal tissue MENT and blood B.

Figure 7:
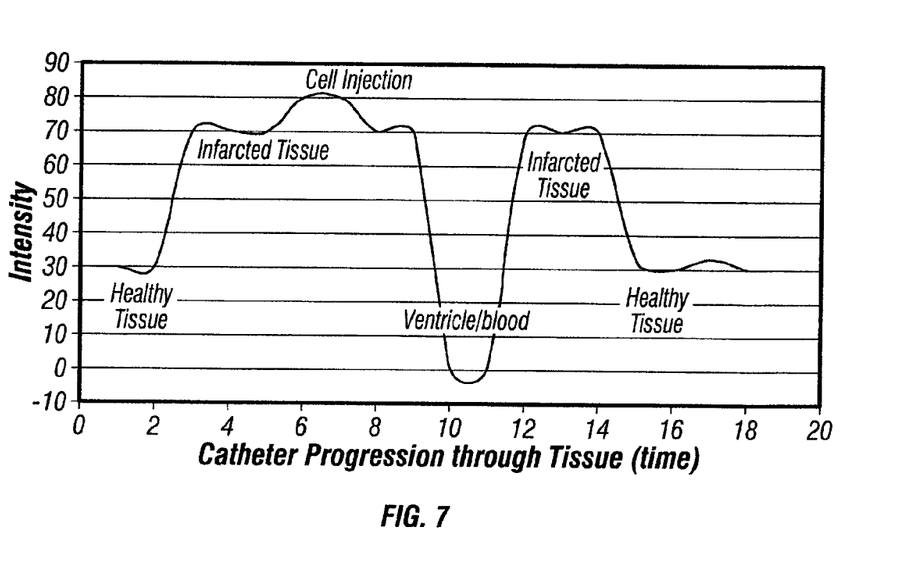
FIG. 7 is a graph showing an example of spectral reflection data generated by an optical sensor equipped catheter as it is advanced into a myocardial infarct and used to deliver a therapeutic or diagnostic substance into that infract.

Spectral reflection may be used to distinguish various types of diseased or pathologically affected tissue from surrounding tissue. FIG. 7 is an example of what an operator might expect to see if he or she were using the invention disclosed herein for intramyocardial cell injections with the horizontal representing units of time measurement and the vertical axis representing units or measurement of light intensity. In the example, an elongate optical device 22, 22a, 22b as described above can be advanced through an infracted myocardial wall while the wavelength of light emitted by the light source 80 remains constant. The computer 84 would provide a graphic display of the intensity of the reflected light relative to the depth of penetration of the elongate optical device 22, 22a, 22b through tissue. In this regard, FIG. 7 shows a graph of intensity versus time generated as the elongate optical device 22, 22a, 22b is advanced transmurally through the infracted ventricular wall from its epicardial surface toward its endocardial surface. Specifically, as seen in FIG. 7, as the device enters the myocardium it initially advances through normal or healthy myocardial tissue (T=1 to 2.5) thus resulting in a reflected signal intensity of approximately 30. Thereafter, as the device continues to advance, it progresses into infracted tissue (T=2.5 to 8.5) as indicated by a substantial increase in the intensity of the reflected light. While positioned within this infarct zone, a desired therapeutic or diagnostic substance (e.g., a medication or cell preparation such as cardiac myocytes or cardiac stem cells suspended in a solution) is injected through a working lumen of the device, thus resulting in an injection artifact or rounded peak (at T=6.2).

In many clinical settings, after the desired diagnostic or therapeutic substance has been injected into the infarct zone, it will be desirable to simply withdraw the device. However, this example, shows what an operator would expect to see if after the substance is injected into the infarct zone, the device was further advanced all the way through the myocardial wall and into the ventricle. In this regard, as shown in FIG. 7 (at T=8.5 to 10.2), when the distal end of the device advances through the endocardium and into a ventricle of the heart, the signal the intensity of reflected light falls precipitously, thereby providing a clear indication that the device has entered a chamber of the heart. This ability to detect entry into the cardiac chamber may be particularly useful in enabling operators to avoid inadvertent injection of a particular substance into the patient's bloodstream. For example, if, during the initial insertion of the device, the intensity of the reflected light falls to a level that is consistent with liquid or blood, the operator will know that the distal end of the device has been advanced too far and has entered the blood-filled cardiac chamber. The operator may then pull the device back and/or reinsert the device to a position where the intensity of the reflected light indicates that the distal end of the device is positioned within the infarct zone, prior to injecting the diagnostic or therapeutic substance. This may be particularly important when the substance being injected would cause clotting of the blood or other systemic toxicities if injected directly into the chamber of the heart or into the patient's bloodstream. On the other hand, this ability to detect entry into the cardiac chamber may also be used for purposeful delivery of a substance into the cardiac chamber or blood stream such as when emergent intra-cardiac drug injection is desired.

In the example of FIG. 7, after the device has been demonstratively advanced into the ventricle, it is retracted back through the infarct zone (from T=12 to 14.2), back through healthy myocardial tissue (from T=14.2 to T=18) and is then removed. Although this example demonstrates the use of spectral reflectance to distinguish between healthy myocardium, infracted myocardium and blood, the same method may be used to distinguish between other types of tissue. For example, this technique may also be used to differentiate between edematous brain tissue and normal brain tissue. See, Thiagrajah, J. R., et al.; *Noninvasive Early Detection of Brain Edema in Mice by Near-Infrared Light Scattering*; Journal of Neuroscience Research 80:293-299 (2005)

Figure 8:
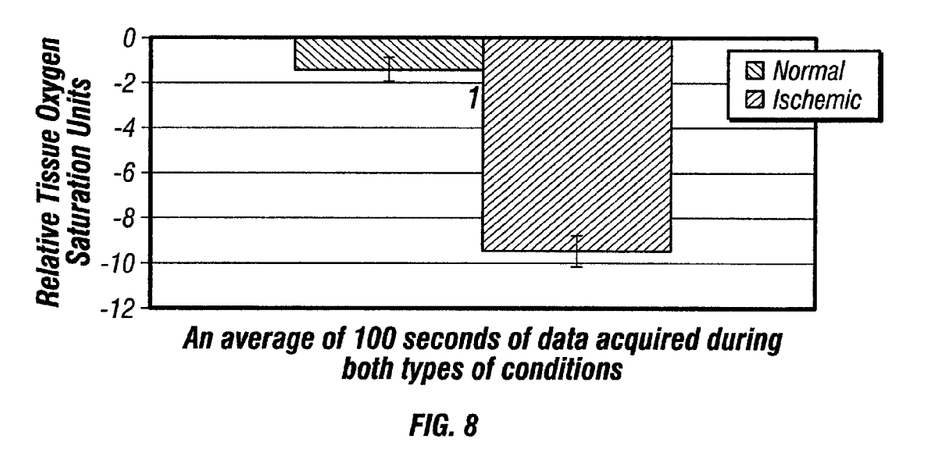
FIG. 8 is a bar graph comparing myocardial tissue oxygen saturation levels in normal and ischemic myocardium using one embodiment of an optical sensor equipped elongate device (e.g., guidewire or catheter) of the present invention.

Although the above-described examples utilize spectral reflection, it is to be appreciated that the specialized optical sensors capable of measuring specific tissue variables (e.g., oxygen saturation, pH, temperature) may be used as well. For example, in some embodiments, the elongate optical device 22, 22a or 22b may comprise an optical sensor attached to or mounted on an optical fiber and the spectrophotometer or other processing device 82 may be specifically designed to receive signals from that optical sensor and to provide, on the basis of such received signals, a reading of the sensed tissue variable. Some non-limiting examples of the manner in which optical sensors may be mounted on optical fibers for use in this invention are described in U.S. Pat. No. 7,209,606 (Cantin, et al.), which is expressly incorporated herein by reference. An example of this approach is seen in FIG. 8, wherein an optical oxygen sensor was used to measure tissue oxygen levels in normal and ischemic myocardium of an open chest pig. In this example, an elongate optical device 22 having a commercially available fiber optic oxygen-sensor (FOXY Oxygen Sensor # 18G available from available from Ocean Optics, Inc., 830 Douglas Ave, Dunedin, Fla. 34698) was mounted inside the tip of an 18 gauge needle and the needle was then advanced into the myocardium. The sensor was calibrated using 37-degree nitrogen purged air as the 0% oxygen standard and the arterial blood of the pig was accessed and served as the 100% oxygen standard. The elongate optical device 22 was inserted into the anterior free wall of the left ventricle and allowed to stabilize. After a few minutes of data recording, the diagonal vessels of the LAD were sutured to create an ischemic zone where the probe was placed. FIG. 8 shows the difference in relative tissue oxygen saturation levels over a period of 100 seconds when the distal tip of the device 22 is positioned within normal and acutely ischemic myocardial tissue.

Techniques have been established for using MRI or NIR to classify tissues as either viable, edematous or necrotic based on the amount of water present in the tissue. S. Merrit, et al., *Coregistration Of Diffuse Optical Spectroscopy And Magnetic Resonance Imaging In A Rat Tumor Model*, Appl Opt. 1; 42(16):2951-9 (June 2003). These techniques may be used in the present invention to guide a delivery catheter or other treatment device to a desired target location within tissue that is affected by a particular pathology (e.g., necrotic tissue, tumor tissue, etc.). The wavelength of the interrogating light may be varied to optimize the system for locating specific types of tissue. For example, Table 1 below summarizes certain wavelengths that may be used for purposes of distinguishing certain types of tissues. The signal intensities at the wavelengths shown in Table 1 are proportional to the pathology. For example, a very distinct peak at 600 nm in a chronic myocardial infarction would indicate scarred tissue.

TABLE 1

| Pathology | Wavelength |
| --- | --- |
| Chronic myocardial infarction (scarred tissue) | 600 nm |
| Acute myocardial infarction (tissue water content characteristic of acutely infracted myocardium) | 975 nm |
| Cancer (tissue water content characteristic of tumor) | 975 nm |
| Stroke | 600 nm |

Further details regarding the use of optical spectroscopy to distinguish tissues based on edema or water content are available in various publications including Nighswander-Rempel S. P., et al., *Regional Variations In Myocardial Tissue Oxygenation Mapped By Near-Infrared Spectroscopic Imaging*, J Mol Cell Cardiol.; 34(9): 1195-203 (September 2002); Merritt S, et al., *Coregistration Of Diffuse Optical Spectroscopy And Magnetic Resonance Imaging In A Rat Tumor Model*, Appl Opt., 1; 42(16): 2951-9 (June 2003) and Cuccia D. J., et al., *In Vivo Quantification Of Optical Contrast Agent Dynamics In Rat Tumors By Use Of Diffuse Optical Spectroscopy With Magnetic Resonance Imaging Coregistration*, Appl Opt., 1; 42(16): 2940-50 (June 2003).

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example described herein may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A method for delivering a diagnostic or therapeutic treatment, substance or device to a myocardial infarct zone located within the myocardium of the heart of a human or animal subject, said method comprising the steps of:
   (A) obtaining or providing an elongate optical device having a single elongate shaft through which a lumen, a light transmitting fiber and a reflected light return fiber extend, said optical device being usable for optical determination of a tissue variable that distinguishes the myocardial infarct zone from other areas of the myocardium and the chambers of the heart;
   (B) obtaining or providing a tissue penetrating catheter device comprising i) a catheter shaft that is positionable in a blood vessel lumen within the subject's body, ii) a penetrator that consists of a single elongate penetrator shaft advanceable in a lateral direction from the catheter shaft to a location outside of the blood vessel lumen in which the catheter shaft is positioned and iii) an orientation indicator useable for predicting the lateral direction in which the single elongate penetrator shaft will subsequently advance, said penetrator having a lumen with a distal opening through which the single elongate shaft of the optical device is advanceable;
   (C) positioning the tissue penetrating catheter device within a blood vessel lumen and using the orientation indicator to adjust the rotational orientation of the catheter shaft within the blood vessel lumen as needed to increase the likelihood that the penetrator will subsequently advance in the direction of the myocardial infarct zone;
   (D) advancing the penetrator laterally from the catheter shaft to a position outside the blood vessel lumen in which the tissue penetrating catheter device is positioned, thereby creating a single penetration tract;
   (E) advancing the single shaft of the elongate optical device through the lumen of the penetrator, out of the distal opening and through tissue in the direction of the myocardial infarct zone, thereby forming a further single penetration tract beyond a distal end of the penetrator;
   (F) delivering light through the light transmitting fiber and using reflected light received from the reflected light return fiber while advancing the optical device to measure said tissue variable and if the measured variable indicates that the device has entered a chamber of the heart, withdrawing the device back into the myocardium;
   (G) determining when said tissue variable indicates that the elongate optical device is within the myocardial infarct zone; and
   (H) delivering a diagnostic or therapeutic modality, substance or device through the lumen of the elongate optical device and into the myocardial infarct zone.

2. A method according to claim 1 wherein the distinguishing variable is selected from the group consisting of: pH, concentration of hydrogen ions, oxygen concentration, dissolved oxygen concentration, temperature and spectral reflection data that matches known spectral reflection data for a type of tissue that is present in a target area.

3. A method according to claim 1 wherein the elongate optical device comprises a guidewire and wherein Step H comprises i) advancing a treatment catheter over the guidewire and into the myocardial infarct zone and ii) using said treatment catheter to deliver a diagnostic or therapeutic treatment, substance or device to the target area.

4. A method according to claim 1 wherein the elongate optical device comprises a delivery catheter.

5. A method according to claim 1 wherein Step H comprises delivering a substance selected form the group consisting of: drugs, thrombolytics, platelet inhibitors, anti-restenotic agents, beta blockers, ion channel antagonists, positive or negative ionotropic agents, anti-arrhythmics, antibiotics, analgesics, chemotherapeutic agents, anti-neoplastic agents, natural or recombinant proteins, angiogenic proteins, vascular endothelial growth factor (VEGF), fibroblast growth factors (FGF), epidermal growth factor (EGF), platelet-derived growth factor (PDGF), nerve cell growth factor (NGF), hepatocyte growth factor (HGF)), cells, cellular preparations, adult stem cells, embryonic stem cells, progenetor cells, myocytes, myoblasts, pancreatic islet cells, dopamine secreting cells, genes, gene therapy preparations, viral vectors containing genes, genetic material for electrophoretic transmission into cells, plasmids, viral vectors, genetically modified cells, naked DNA, contrast media, dyes, radio-labeled diagnostic materials, radiolabled drugs, dialysis solutions, micro-dialysis solutions, radioactive pellets, radiotherapy preparations, radiofrequency absorption enhancers, nanoparticles, carbon nanoparticles, platelet rich plasma, thrombin solution, platelet gel, autologous platelet gel, fillers, bulking agents, collagen, hyaluronic acid and glycosaminoglycans.

6. A method according to claim 4 wherein the delivery catheter has a plurality of working lumens and wherein Step H comprises delivering a plurality of substances, in separate streams, through said plurality of working lumens such that said plurality of substances become combined within the myocardial infarct zone.

7. A method according to claim 6 wherein said plurality of substances comprises i) platelet rich plasma and ii) a thrombin containing solution which become combined to form platelet gel within the myocardial infarct zone.

8. A method according to claim 1 wherein the myocardial infarct zone comprises scar tissue and the interrogating light delivered through the optical fiver has a wavelength of 600 nm.

9. A method according to claim 1 wherein Step H comprises using the elongate optical device to facilitate delivery of a device selected from the group consisting of: substance eluting implants, radioactive implants, embolic members, markers, radiopaque markers, catheters, cannulae, wires, electrodes, sensors and implants.

10. A method according to claim 1 wherein the orientation indicator comprises an intravascular ultrasound device.

* * * * *